United States Patent [19]

Nysted

[11] 3,960,904

[45] June 1, 1976

[54] 6-AMINOMETHYLATED 3-OXYGENATED CHOLEST-5-ENES

[75] Inventor: Leonard N. Nysted, Highland Park, Ill.

[73] Assignee: G. D. Searle & Co., Chicago, Ill.

[22] Filed: June 6, 1975

[21] Appl. No.: 584,512

[52] U.S. Cl. .............................. 260/397.2; 424/238
[51] Int. Cl.² ........................................... C07J 9/00

[58] Field of Search ................................. 260/397.2

*Primary Examiner*—Elbert L. Roberts
*Attorney, Agent, or Firm*—John M. Brown

[57] ABSTRACT

Preparation of analgesic, antisecretory, antiulcerogenic, hypolipemic, and antimicrobial 6-aminomethylated 3-oxygenated cholest-5-enes is disclosed.

14 Claims, No Drawings

6-AMINOMETHYLATED 3-OXYGENATED CHOLEST-5-ENES

This invention relates to 6-aminomethylated 3-oxygenated cholest-5-enes and processes for the preparation thereof. More particularly, this invention provides new, useful, and unobvious bases of the formula

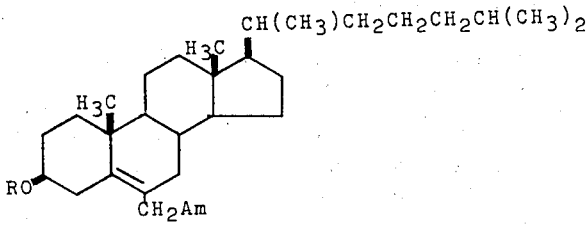

wherein R represents hydrogen, alkanoyl, or alkanesulfonyl and AM represents amino, dialkylamino, di(hydroxyalkyl) amino, or di(alkoxyalkyl)amino.

Among the alkanoyls comprehended by R, lower alkanoyls are preferred, i.e., radicals of the formula

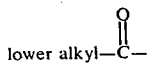

wherein the lower alkyl is methyl, ethyl, 1-methylethyl, 1,1-dimethylethyl, propyl, 1-methylpropyl, 2-methylpropyl, 2,2-dimethylpropyl, butyl, pentyl, 4-methylpentyl, hexyl, 3-methylhexyl, heptyl, or like monovalent, saturated, acyclic, straight- or branched-chain, hydrocarbon grouping of the formula

in which $n$ represents a positive integer less than 8.

The alkanesulfonyls comprehended by R are, preferably, radicals of the formula

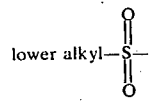

wherein the lower alkyl constituent is defined as above. Among such radicals, methanesulfonyl is especially preferred.

The dialkylaminos comprehended by Am are preferably radicals of the formula $$-N(\text{lower alkyl})_2$$

wherein the lower alkyl constituents are defined as above.

The di(hydroxyalkyl)aminos comprehended by Am are preferably radicals of the formula

wherein $n$ is defined as above. Among such radicals, those in which each of the 2 hydroxyalkyls called for contain more than 1 and fewer than 5 carbons are especially preferred. As the formula indicates, the hydroxyl constituent of each hydroxyalkyl can be attached to any one of a plurality of carbons therein.

The di(alkoxyalkyl)aminos comprehended by Am are preferably radicals of the formula $$-N(C_xH_{2x}OC_yH_{2y+1})_2$$

wherein $x$ and $y$ represent positive integers less than 8 — especially more than 1 and less than 4, and more than 1 and less than 5, respectively. The alkoxy constitutent of each alkoxyalkyl can be attached to any one of a plurality of carbons in the remainder of the alkoxyalkyl grouping.

Equivalent to the foregoing bases for the purposes of this invention are non-toxic acid addition and quaternary ammonium salts thereof having the formula

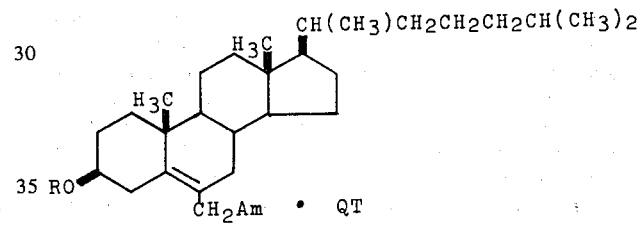

wherein R and Am are defined as above; Q represents hydrogen, lower alkyl, hydroxy(lower alkyl), lower alkenyl such as vinyl and allyl, or aralkyl such as benzyl and phenethyl; and T represents 1 equivalent of an anion — for example, fluoride, bromide, iodide, nitrate, phosphate, sulfate, sulfamate, methyl sulfate, ethyl sulfate, benzenesulfonate, toluenesulfate, acetate, lactate, succinate, maleate, tartrate, citrate, gluconate, ascorbate, benzoate, cinnamate, or the like — which, in combination with the cationic portion of a salt aforesaid, is neither biologically nor otherwise incompatible.

The compounds of this invention are useful by reason of their valuable biological properties. Thus, for example, they are antimicrobial agents: They inhibit or prevent the growth of bacteria such as *Staphylococcus aureus, Salmonella paratyphi A, Propionobacterium acnes, Clostridium perfringens, Fusobacterium necrophorum,* and *Erwinia sp.*; protozoa such as *Tritrichomonas foetus, Trichomonas vaginalis, Tetrahymena pyriformis,* and *Pentatrichomonas hominis;* fungi such as *Trichophyton mentagrophytes, Candida albicans,* and *Verticillium albo-atrum;* and algae such as *chlorella vulgaris.* Other biological properties of compounds of this invention include analgesic, antisecretory, antiulcerogenic, and hypolipemic activity.

The utility of the instant compounds in respect of *S. paratyphi A*, *T. mentagrophytes*, *V. albo-atrum*, and *C. vulgaris* can be demonstrated by standardized tests described in U.S. Pat. No. 3,679,697. Utility in respect of *C. perfringens*, *T. foetus*, and *P. hominis* can be demonstrated by standardized tests described in U.S. Pat. No. 3,882,136. Utility in respect of *Erwinia sp.*, *T. vaginalis* and *T. pyriformis* can be demonstrated by standardized tests described in U.S. Pat. No. 3,663,647.

The utility of the instant compounds in respect of *S. aureus* can be demonstrated via the following standardized test: Nutrient broth (manufactured by Baltimore Biological Laboratories or Difco) is prepared as recommended by the manufacturer, sterilized, and inoculated with *S. aureus* ATCC 6538 q.s. 1 million cells per ml, determined spectrophotometrically. Meanwhile, compound is heated in sterile distilled water at a concentration of 1000 mcgm per ml for 20 minutes at 80°C. This compound preparation is serially diluted and mixed with sufficient inoculated medium to afford concentrations of 100, 10, 1, and 0.1 mcgm of compound per ml. The mixtures thus obtained are incubated aerobically for 20–24 hr at 37°C and then examined grossly for growth of the organism. Controls are provided by concurrent incubations identical with the above except that (1) reference standards (4.3, 0.43, 0.043, and 0.0043 mcgm per ml of streptomycin sulfate and 6667, 667, 67, and 7 units of potassium penicillin G) are substituted for compound and (2) neither compound nor reference standard is present. Compounds are considered active if, at the maximum concentrations tested, no growth of organism is observed and no aberrancy is apparent in respect of the controls. Potency is expressed as the minimum concentration at which a compound is active.

The utility of the instant compounds in respect of *P. acnes*, can be determined by a standardized test identical with the one described in the paragraph immediately preceding except that fluid thioglycollate medium (manufactured by Baltimore Biological Laboratories or Difco) is substituted for nutrient broth and *P. acnes* ATCC 6919 [originally isolated from clinical cases of acne vulgaris; see J. Bacteriol., 52, 15(1946)] is substituted in *S. aureus*. The utility of the instant compounds in respect of *F. necrophorum* can be demonstrated by a standardized test identical with the one described in the paragraph immediately preceding except that *F. necrophorum* ATCC 25286 is substituted for *S. aureus*.

The utility of the instant compounds in respect of *C. albicans* can be demonstrated via the following standardized test: Yeast nitrogen base [manufactured in accordance with J. Bacteriol., 56, 363 (1948)] is prepared as recommended by the manufacturer, sterilized, and inoculated with *C. albicans* ATCC 10231 q.s. one million cells per ml, determined spectrophotometrically. Meanwhile, compound is heated in sterile distilled water at a concentration of 1000 mcgm per ml for 20 minutes at 80°C. This compound preparation is serially diluted and mixed with sufficient inoculated medium to afford concentrations of 100, 10, 1, and 0.1 mcgm of compound per ml. The mixtures thus obtained are incubated aerobically for 20–24 hr at 37°C and then examined grossly for growth of the organism. Controls are provided by concurrent incubations identical with the above except (1) reference standards (100, 10, 1, and 0.1 mcgm ml of nystatin and, separately, of amphotericin B) are substituted for compound and (2) neither compound nor reference standard is present. Compounds are considered active if, at the maximum concentrations tested, no growth of organism is observed and no aberrancy is apparent in respect of the controls. Potency is expressed as the minimum concentration at which a compound is active.

The product of Example 3A hereinafter, a preferred embodiment of this invention, was active at concentrations of 1 mcgm per ml versus *P. acnes* and *Erwinia sp.*; 10 mcgm per ml versus *C. perfringens*, *F. necrophorum*, *T. foetus*, *T. vaginalis*, *t. pyriformis*, *P. hominis*, and *C. vulgaris*; 100 mcgm per ml versus *V. albo-atrum*; and 1000 mcgm per ml versus *S. paratyphy A.* and *T. mentagrophytes* in the foregoing antimicrobial tests. The product of Example 6A hereinafter, another preferred embodiment of the invention, was active at concentrations of 1 mcgm per ml versus *P. acnes* and *C. albicans*; 10 mcgm per ml versus *S. aureus*, *C. perfringens*, *T. foetus*, *T. vaginalis*, *T. pyriformis*, *V. albo-atrum*, and *C. vulgaris*; and 100 mcgm per ml versus *F. necrophorum*, *P. hominis*, and *T. mentagrophytes* in said tests.

Analgesic utility can be demonstrated via the standardized test described in U.S. Pat. No. 3,663,547. The product of Example 6A hereinafter was active at 25 mg per kg in this test.

Antisecretory utility can be demonstrated by a standardized test for the capacity to decrease stomach acid and/or protease activity in rats subjected to fasting and pyloric ligation substantially as described by Shay et al. in Gasteroenterology, 5, 43 (1945). In this test, male Charles River rats weighing 200–250 gm are fasted in individual cages for 48 hr and then lightly anesthetized with ether. Midline abdominal incisions are made and the pylori ligated. Immediately following ligation, the prescribed dose of compound, dissolved or suspended in 1.0 ml of water, is intragastrically administered to each of a group of 6 animals. Another group of 6 animals, to each of which is concurrently and identically administered 1.0 ml of plain water, serves as controls. Incisions are clamped shut and coated with collodian, whereupon the animals are returned to their cages. Precisely 5 hours after the initial anesthesia, the animals are chloroformed to incipient death; and incisions are made through which the esophagi are clamped shut and the stomachs removed by cutting below the ligatures and above the clamps. Free acids in the gastric contents are thereupon individually determined, for both the animals to which compound was administered (treats) and the controls, by titration with 0.02 N sodium hydroxide to the phenolphthalein end point; while protease activity is assayed in each instance via a technique derived from M. L. Anson in J. Gen. Physiol., 22, 79 (1938) which depends on the fact that proteolysis results in liberation of peptides containing tyrosine and tryptophan units characterized by an absorption band in the ultraviolet spectrum at 275 m$\mu$. Absorption at this wavelength serves therefore as an index of the extent to which the proteolysis has occurred. The protease assay is carried out in test tubes, a treat tube containing 0.1 ml of gastric juice, 1.9 ml of pH 2.0 hydrochloric acid, and 5 ml of aqueous 1.65% hemoglobin solution, together with a control tube containing 0.1 ml of gastric juice and 6.9 ml of pH 2.0 hydrochloric acid, being prepared for each test animal. The tubes are promptly and simultaneously incubated at 37°C. for 110 minutes, whereupon enzyme activity therein is immediately terminated by adding to each tube 1 ml of pH 2.0 hydrochloric acid and 1 ml of 20% perchloric acid. Contents of the tubes are separately filtered, and 1 ml of each filtrate is mixed with 10 ml of pH 5.0 sodium acetate buffer prepared by adjustment of the pH of a mixture of 25.45 ml glacial acetic acid and 4000 ml of double distilled water with aqueous 6 N sodium hydroxide. The resultant solutions are subjected to spectrophotometric analyses whereby the absorptions at 275m$\mu$ determined. A compound is considered antisecretory if the mean treat value for either free acid (expressed in milliequivalents) or absorption (expressed as optical density) is significantly (P $\leq$ 0.05, Student's t-test) less than the corresponding mean control value. The product of Example 6A hereinafter was active at the 5 mg dose level in this test.

Antiulcerogenic activity can be demonstrated via the standardized test described in U.S. Pat. No. 3,483,192. The product of Example 3A hereinafter was active at the 5 mg dose level in this test.

Hypolipemic activity can be demonstrated via the two standardized tests therefor described in U.S. Pat. No. 3,843,660. In the first of said tests, the product of Example 6A hereinafter was active at 100 mg per kg.

Those skilled in the art will recognize that observations of activity in standardized tests for particular biological effects are fundamental to the development of valuable new drugs, both veterinary and human. Distinct from such application, antialgal compounds are adapted to the conditioning of boiler feed water and the like.

Preparation of the compounds of this invention proceeds from 3$\beta$-acetoxy-5$\alpha$-hydroxycholestan-6-one [Shionogi Kenkusho Nempo, 10, 47 (1960)], which is contacted with the complex (U.S. Pat. No. 3,634,469, Example 2) formed in situ by heating activated zinc with dibromomethane in tetrahydrofuran under nitrogen, using aluminum isopropoxide to catalyze the complex formation. The resultant 3$\beta$-acetoxy- 6- methylenecholestan-5$\alpha$-ol is converted to 3$\beta$-acetoxy-6-(bromomethyl/chloromethyl)cholest-5-ene by contacting in cold dichloromethane with the appropriate phosphorus trihalide. The 6- halomethyl compound (commonly 6-bromo because of the lesser reaction time and temperature which its greater reactivity permits) is contacted with an amine of the formula AmH wherein Am is defined as above. Contact is effected at elevated pressures when the amine is ammonia, at elevated temperatures when interaction of the 6- halomethyl compound and amine is thereby facilitated, and in the presence of solvent when the interactants are otherwise immiscible. The 3$\beta$-acetate thus obtained (having the formula

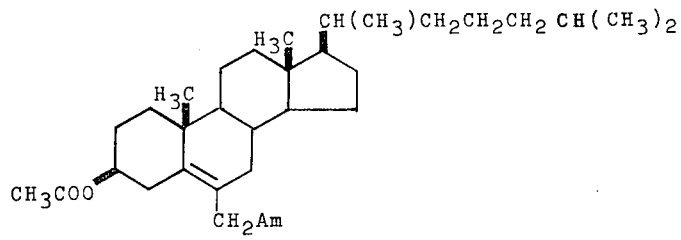

wherein Am is defined as above) can be heated with methanolic potassium bicarbonate or contacted with methanolic hydrogen chloride to cleave the ester linkage. (The latter procedure affords a hydrochloride which, like any of the acid addition salts of the invention, can be converted to the corresponding base by contacting with excess alkali). Contacting a 3$\beta$-ol of the invention in cold pyridine with an alkanoyl or alkanesulfonyl chloride, followed by alkalization, affords a corresponding basic ester of the invention. From the bases hereof, upon simple admixture with 1 equivalent of any of various inorganic and strong organic acids wherein the anionic moiety can be represented by T as defined above, the acid addition salts of the invention can be obtained. Alternatively, the bases can be converted to quaternary ammonium compounds of the invention by contacting in an inert solvent such as chloroform, acetone, butanone, or methanol with 1 equivalent of an organic ester of the formula

Q'T wherein the definition of Q' is identical with that of Q above, excepting that Q' does not represent hydrogen, and T is defined as before. Quaternarzation is commonly carried out at temperatures ranging from 5° to 100°C in from 1 hr to 5 days, a closed system being used if the involved ester is a gas at operating temperatures. Quaternary ammonium compounds of this invention can also be prepared by contacting 3$\beta$-acetoxy-6-(bromomethyl/chloromethyl)cholest-5-ene with a trialkylamine, tri(hydroxyalkyl)amine, or tri(alkoxyalkyl)amine, using a solvent medium if required for homogeneity, and cleaving the ester linkage in the product if desired by heating it with methanolic hydrogen halide.

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set forth, temperatures are given in degrees centigrade and relative amounts of materials in parts by weight, except as otherwise noted.

EXAMPLE 1

A. To a mixture of 65 parts of powdered zinc and 145 parts of tetrahydrofuran at the boiling point under reflux in a nitrogen atmosphere is added, with stirring during 10 minutes, 35 parts of a 20% solution of hydrogen chloride in dioxane, followed after 20 minutes by 5 parts of aluminum isopropoxide. Approximately 5 minutes later, introduction of 70 parts of dibromomethane is commenced, the rate being such as to require approximately 2½ hours for completion. Heating at the boiling point under reflux with stirring is continued throughout this operation and for approximately 14 hours thereafter, at which point the temperature of the reaction mixture is lowered to −10° and 42 parts of 3β-acetoxy-5α-hydroxycholestan-6-one is stirred in during 10 minutes. The reaction mixture is then warmed to room temperature during 1 hour and maintained thereat for a further 2 hours, stirring being continued throughout. At this point the temperature of the reaction mixture is again lowered, this time to around 5°, at which temperature 100 parts of aqueous 50% acetic acid is added — slowly for as long as gas evolution continues and rapidly thereafter. The temperature of the reaction mixture rises too around 28° during this operation. Insoluble solids are filtered out, and the filtrate is vigorously steam-distilled until the tacky solids which precipitate in the distilland become crystalline. The crystalline material is filtered from the hot distilland, washed with water, and sufficiently dried to be taken up in approximately 65 parts of dichloromethane. The dichloromethane solution is filtered through diatomaceous earth, which is then washed with 140 parts of acetone. Washings and filtrate are combined and distilled while 175 parts of water is slowly added. Crystallization occurs. Distillation is continued for a short time thereafter, whereupon the crystals are filtered off, washed well with aqueous 50% acetone, and dried in vacuo at 60°. The product thus isolated is 3β-acetoxy-6-methylenecholestan-5α-ol.

B. To a solution of 12 parts of phosphorus tribromide in 65 parts of dichloromethane at 0° is slowly added, with stirring, a solution of 12 parts of 3α-acetoxy-6-methylenecholestan-5α-ol in 65 parts of dichloromethane. When the addition is complete, stirring is continued while the temperature of the reaction mixture is increased to approximately 25° during 30 minutes. At this point, 105 parts of diethyl ether, followed — cautiously — by 100 parts of aqueous 10% sodium dicarbonate is mixed in. The organic phase is then separated, washed with aqueous 10% potassium bicarbonate, dried over anhydrous sodium sulfate, and stripped of solvent by vacuum distillation. The residue is 3β-acetoxy-6-(bromomethyl)cholest-5-ene, which is further purified by trituration with 40 parts of methanol.

C. A mixture of 10 parts of 3β-acetoxy-6-(bromomethyl)cholest-5-ene, 14 parts of liquid ammonia, and 90 parts of benzene is stirred at room temperature in a sealed vessel for 24 hours, whereupon excess ammonia is vented and 50 parts of aqueous 10% potassium bicarbonate then introduced. The benzene phase is separated, washed with water, dried over anhydrous sodium sulfate, and stripped of solvent by vacuum distillation. The residue is 3β-acetoxy-6-(aminomethyl)cholest-5-ene, having the formula

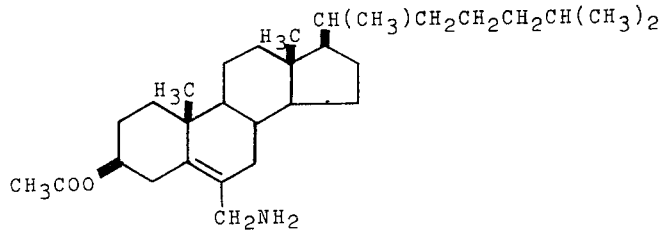

D. A solution of 1 part of 3β-acetoxy-6-(aminomethyl)cholest-5-ene- in a minimal volume of hexane is acidified with acetic acid. The solid which precipitates is filtered off, washed with hexane, and dried in air. The product thus isolated is 3β-acetoxy-6-(aminomethyl)-cholest-5-ene acetate.

EXAMPLE 2

A solution of 11 parts of 3β-acetoxy-6-(bromomethyl)cholest-5-ene and 9 parts of dimethylamine in 45 parts of benzene is maintained at 50° in a sealed vessel for 24 hours, whereupon volatile components are removed by vacuum distillation and the residue extracted with hexane. The extract is filtered, and the filtrate is stripped of solvent by vacuum distillation. The residue is 3β-acetoxy-6-(dimethylaminomethyl)cholest-5-ene, having the formula

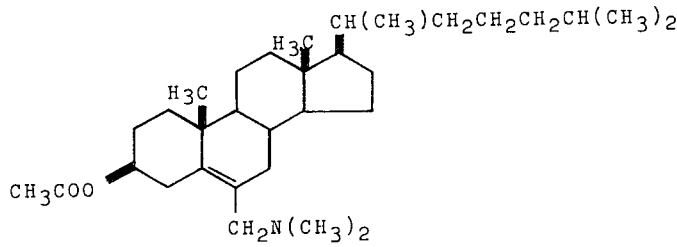

EXAMPLE 3

A. A solution 10 parts of 3β-acetoxy-6-(dimethylaminomethyl)cholest-5-ene in 40 parts of methanol is acidified with a 20% solution of hydrogen chloride in dioxane. The resultant mixture is allowed to stand at room temperature for 24 hours, whereupon sufficient ether is added to induce precipitation. The precipitate is filtered off, washed with ether, and dried in air. The product thus isolated is 6-(dimethylaminomethyl)cholest-5-en-3β-ol hydrochloride hemihydrate, from which the water of crystallization can be removed by heating in vacuo above 100°.

B. Approximately 5 parts of 6-(dimethylaminomethyl)-cholest-5-en-3β-ol hydrochloride hemihydrate is partitioned between 70 parts of diethyl ether and a solution of 2 parts of sodium hydroxide in 75 parts of water. The ethereal phase is separated, washed with water, and stripped of solvent by vacuum distillation. The residual oil is 6- (dimethylaminomethyl)cholest-5-en-3β-ol.

C. Approximately 5 parts of methyl bromide is introduced beneath the surface of a solution of 3 parts of 6-(dimethylaminomethyl)cholest-5-en-3β-ol in 16 parts of 2-butanone. The resultant solution is heated to 50° for 5 minutes, then allowed to stand at room temperatures for 24 hours. The crystalline precipitate which forms is thereupon filtered off, washed with diethyl ether, and dried in vacuo. The product thus isolated is 3β-hydroxy-N,N,N-trimethylcholest-5-ene-6-methanaminium bromide, having the formula

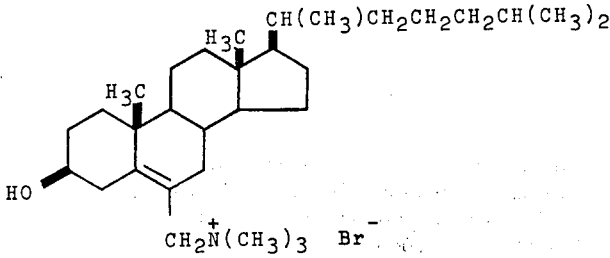

D. A mixture of 4 parts of 6-(dimethylaminomethyl)-cholest-5-ene-3β-ol and 20 parts of phenethyl bromide is heated at 90°–95° for 5 hours. The resultant solid is triturated with ethyl acetate, washed with diethyl ether, and dried in vacuo. The product thus isolated is 3β-hydroxy-N,N-dimethyl-N-phenethylcholest-5-ene-6-methanaminium bromide.

EXAMPLE 4

To a solution of 6 parts of 6-(dimethylaminomethyl)-cholest-5-en-3β-ol in 100 parts of pyridine at −10° is added, with stirring during 10 minutes, 15 parts of methanesulphonyl chloride. The resultant mixture is stirred at −10° for 2½ hours, whereupon 200 parts of ice, 140 parts of diethyl ether, and sufficient aqueous 25% potassium carbonate for basicity are consecutively stirred in. The ethereal phase is separated, washed with water, dried over, anhydrous sodium sulfate, and stripped of solvent by vacuum distillation. The residue is recrystallized from a mixure of dichloromethane and hexane. The product thus obtained is 3β-(methanesulphonyloxy)-6-(dimethylaminomethyl)-cholest-5-ene, having the formula

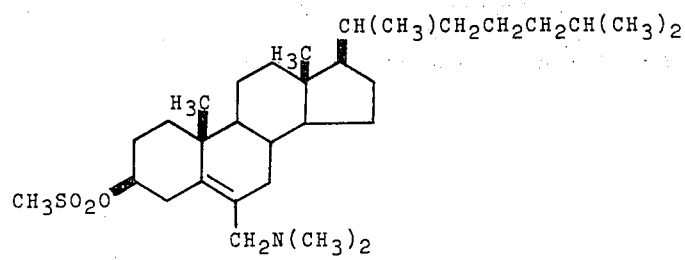

EXAMPLE 5

A. Substitution of 6 parts of phosphorus trichloride for the phosphorus tribromide called for in Example 1B affords, by the procedure there detailed, 3β-acetoxy-6-(chloromethyl)cholest-5-ene.

B. Substitution of 10 parts of 3β-acetoxy-6-(chloromethyl)cholest-5-ene and 14 parts of diethylamine for the 3β-acetoxy-6-(bromomethyl)cholest-5-ene and dimethylamine, respectively, called for in Example 2 affords, by the procedure there detailed, 3β-acetoxy-6-(diethylaminomethyl)cholest-5-ene.

EXAMPLE 6

A. Substitution of 10 parts of 3β-acetoxy-6-(diethylaminomethyl)cholest-5-ene for the 62 -acetoxy-6-(dimethylaminomethyl)cholest-5-ene called for in Example 3A affords, by the precedure there detailed, 6-(diethylaminomethyl)cholest-5-en-3β-ol hydrochloride melting at 234°–236° with decomposition.

B. Substitution of 5 parts of 6-(diethylaminomethyl)-cholest-5-en-3β-ol hydrocholoride for the 6-(dimethylaminomethyl)cholest-5-en-3β-ol hydrocholoride hemihydrate called for in Example 3B affords, by the procedure there detailed, 6-(diethylaminomethyl)cholest-5-en-3β-ol.

EXAMPLE 7

To a solution of 10 parts of 6-(diethylaminomethyl)-cholest-5-en-3β-ol in 40 parts of pyridine at 0° is added, slowly and with stirring, 5 parts of propionyl chloride. When the addition is complete, stirring is continued for 2 hours while the reaction mixture warms to room temperature, whereupon 100 parts of water and 100 parts of aqueous 5% potassium bicarbonate are consecutively mixed in. The oil which separates is extracted with hexane. The extract is washed with water, dried over anhydrous sodium sulfate, and stripped of solvent by vacuum distillation, affording 6-(diethylaminomethyl)-3β-(propionyloxy)cholest-5-ene as the residue.

EXAMPLE 8

A mixture of 10 parts of 3β-acetoxy-6-(chloromethyl)cholest-5-ene and 8 parts of dibutylamine is heated at 90°–95° for 3 hours, whereupon excess amine is removed by vacuum distillation and the residue is extracted with hexane. The extract is washed with water, dried over anhydrous sodium sulfate, and stripped of solvent by vacuum distillation, affording 3β-acetoxy-6-(dibutylaminomethyl)cholest-5-ene as the residue.

EXAMPLE 9

A. A mixture of 15 parts of 3β-acetoxy-6-(chloromethyl)cholest-5-ene and 20 parts of diethanolamine is heated to 95°, then allowed to cool to 65°and maintained thereat for 24 hours. At this point 50 parts of water is introduced, and the resultant mixture is extracted with diethyl ether. The extract is washed with water, dried over anhydrous sodium sulfate, and stripped of solvent by vacuum distillation. The residue, an oil, is 3β-acetoxy-6-[di(2-hydroxyethyl)aminomethyl]cholest-5-ene, having the formula

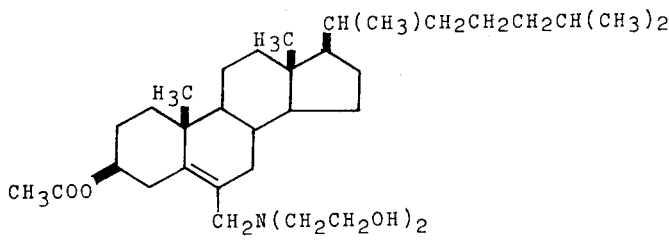

B. To a solution of 3 parts of 3β-acetoxy-6-[di(2-hydroxyethyl)aminomethyl]cholest-5-ene in 16 parts of acetone is added, beneath the surface, 2 parts of methyl bromide. The resultant mixture is allowed to stand at room temperatures for 60 hours, whereupon the solid which separates is filtered off, washed with ethyl acetate, and dried in vacuo. The product thus isolated is 3β-acetoxy-N,N-di(2-hydroxyethyl)-N-methylcholest-5-ene-6-methanaminium bromide.

EXAMPLE 10

To a solution of 10 parts of 3β-acetoxy-6-(bromomethyl)cholest-5-ene in a mixture of 36 parts of benzene and 8 parts of acetone is added 5 parts of triethanolamine. The resultant mixture is allowed to stand at room temperatures for 5 days. The solid which separates is isolated by filtration, washed with a 9:1 mixture of ether and acetone, and dried in vacuo. The product thus isolated is 3β-acetoxy-N,N,N-tri(2-hydroxyethyl)-cholest-5-ene-6-methanaminium bromide.

EXAMPLE 11

A solution of 10 parts of 3β-acetoxy-6-(bromomethyl)cholest-5-ene and 20 parts of bis(ethoxyethyl)amine in 13 parts of dichloromethane is allowed to stand at room temperatures for 24 hours, whereupon 5 volumes of water is introduced and the oil which separates is extracted with diethyl ether. The extract is washed with water, dried over anhydrous sodium sulfate, and stripped of solvent by vacuum distillation to give 3β-acetoxy-6-[di(2-ethoxyethyl)aminomethyl]cholest-5-ene as the residue. The product, an oil, has the formula

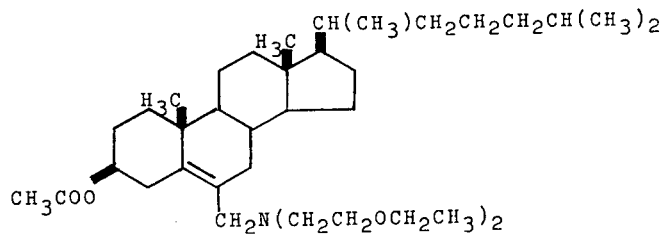

EXAMPLE 12

To a solution of approximately 10 parts of 3β-acetoxy-6-(dibutylaminomethyl)cholest-5-ene in 80 parts of methanol is added 10 parts of aqueous 20% potassium carbonate. The resultant mixture is heated to the boiling point under reflux for 2 hours, whereupon 100 parts of water is introduced. The oil which separates is extracted with hexane. The extract is washed with water, dried over anhydrous sodium sulfate, and stripped of solvent by vacuum distillation. The residual oil is taken up in benzene; and the benzene solution is chromatographed on alumina, using benzene and mixtures thereof with increasing amounts of ethanol as developing solvents. From an eluate comprising 2% ethanol in benzene, on evaporation of solvent, 6-(dibutylaminomethyl)cholest-5-en-3β-ol is obtained as the residue.

EXAMPLE 13

A. A solution of 15 parts of 3β-acetoxy-6-[di(2-hydroxyethyl)aminomethyl]cholest-5-ene in 40 parts of methanol is acidified with a 20% solution of hydrogen chloride in dioxane. The resultant mixture is allowed to stand at room temperatures for 24 hours, whereupon sufficient diethyl ether is introduced to effect precipitation of a solid. The precipitate is isolated by filtration, washed with diethyl ether, and dried in vacuo. The product thus obtained is 6-[di(2-hydroxyethyl)aminomethyl]cholest-5en-3β-ol hydrochloride.

B. Substitution of 5 parts of 6-[di(2-hydroxyethyl)aminomethyl]cholest-5-en-3β-ol hydrochloride for the 6-(dimethylaminomethyl)cholest-5-en-3β-ol hydrochloride hemihydrate called for in Example 3B affords, by the procedure there detailed 6-[di(2-hydroxyethyl)aminomethyl]cholest-5-en-3β-ol.

C. Approximately 3 parts of methyl bromide is bubbled into a solution of 4 parts of 6-[di(2-hydroxyethyl)aminomethyl]cholest-5-en-3β-ol in 16 parts of acetone. The resultant solution is allowed to stand at room temperatures for 24 hours. The crystalline precipitate which forms is filtered off, washed with ethyl acetate, and dried in vacuo. The product thus isolated is 3β-hydroxy-N,N-di(2-hydroxyethyl)-N-methylcholest-5-ene-6-methanaminium bromide.

EXAMPLE 14

A solution of 24 parts of 3β-acetoxy-N,N,N-tri(2-hydroxyethyl)cholest-5-ene-6-methanaminium bromide and 40 parts of hydrogen bromide in 200 parts of ethanol is heated at the boiling point under reflux for 15 minutes. The reaction mixture is thereupon allowed to cool. A crystalline precipitate forms. The precipitate is isolated by filtration, washed with ethyl acetate, and dried in vacuo. The product thus isolated is 3β-hydroxy-N,N,N-tri(2-hydroxyethyl)cholest-5-ene-6-methanaminium bromide.

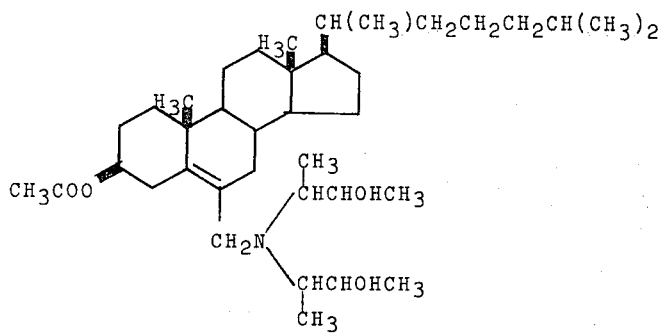

EXAMPLE 15

A. A solution of 10 parts of 3β-acetoxy-6-[di(2-ethoxyethyl)aminomethyl]cholest-5-ene in 20 parts of methanol is acidified with a 20% solution of hydrogen chloride in dioxane. The resultant mixture is allowed to stand for 24 hours, then diluted with 200 parts of water. The solution thus obtained is washed with diethyl ether, then basified with aqueous 20% sodium hydroxide, whereupon the oil which separates is extracted with diethyl ether. The ether extract is consecutively washed with aqueous 5% potassium bicarbonate and water, dried over anhydrous sodium sulfate, and filtered through a mixture of charcoal and infusorial earth. The filtrate is stripped of solvent by vacuum distillation. The residue is 6-[di(2-ethoxyethyl)aminomethyl]cholest-5-en-3β-ol, a viscous oil.

B. Approximately 2 parts of methyl bromide is introduced beneath the surface of a solution of 3 parts of 6-[di(2-ethoxyethyl)aminomethyl]cholest-5-en-3β-ol in 8 parts of acetone. The resultant mixture is allowed to stand at room temperatures for 48 hours, during which an oil separates. Supernatant liquors are decanted from the oil, which is then washed by slurrying in hexane. The hexane is removed by vacuum distillation at 60°, leaving N,N-di(2-ethoxyethyl)-3β-N-methylcholest-5-ene-6methanaminium bromide as the residue.

EXAMPLE 16

Substitution of 20 parts of 3,3'-iminobis(2-butanol) [prepared by heating 2,3-epoxybutane with ammonia at 90°–120° as described in British Pat. No. 710,861, issued June 23, 1954]for the diethanolamine called for in Example 9A affords, by the procedure there detailed, 3β-acetoxy-6-[di(2-hydroxy-1-methylpropyl)aminomethyl]cholest-5-ene having the formula

EXAMPLE 17

A. Substitution of 3β-acetoxy-6-[di(2-hydroxy-1-methylpropyl)aminomethyl]cholest-5-ene for the 3β-acetoxy-6-[di(2-hydroxyethyl)aminomethyl]cholest-5-ene called for in Example 13A affords, by the procedure there detailed, 6-[di(2-hydroxy-1-methylpropyl)aminomethyl]-cholest-5-en-3β-ol hydrochloride.

B. Substitution of 5 parts of 6-[di(2-hydroxy-1-methylpropyl)aminomethyl]cholest-5-ene-3β-ol hydrochloride for the 6-(dimethylaminomethyl)cholest-5-en-3β-ol hydrochloride hemihydrate called for in Example 3B affords, by the procedure there detailed, 6-[di(2-hydroxy-1-methylpropyl)aminomethyl]cholest-5-en-3β-ol.

EXAMPLE 18

Substitution of 20 parts of bis(3-butoxypropyl)amine [U.S. Pat. No. 2,372,624] for the bis(ethoxyethyl)amine called for in Example 11 affords, by the procedure there detailed, 3β-acetoxy-6-[di(3-butoxypropyl)aminomethyl]cholest-5-ene, having the formula

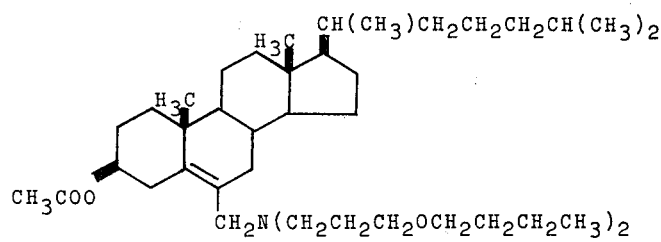

EXAMPLE 19

Substitution of 10 parts of 3β-acetoxy-6-[di(3-butoxypropyl)aminomethyl]cholest-5-ene for the 3β-acetoxy-6-[di(2-ethoxyethyl)aminomethyl]cholest-5-ene called for in Example 15A affords, by the procedure there detailed, 6-[di(3-butoxypropyl)aminomethyl]cholest-5-en-3β-ol.

What is claimed is:

1. A compound of the formula wherein R represents hydrogen, alkanoyl of the formula $C_nH_{2a+1}CO-$ in which $a$ represents a positive integer less than 8, or methanesulphonyl and R' represents hydrogen, alkyl of the formula $C_bH_{2b+1}-$ in which $b$ represents a positive integer less than 8, hydroxyalkyl of the formula $HOC_cH_{2c}-$ in which $c$ represents a positive integer more than 1 and less than 5, or alkoxyalkyl of the formula $C_dH_{2d+1}OC_eH_{2e}-$ in which $d$ represents a positive integer greater than 1 and less than 5 and $e$ represents a positive integer greater than 1 and less than 4.

2. A compound according to claim 1 which is 3β-acetoxy-6-(aminomethyl)cholest-5-ene.
3. A compound according to claim 1 having the formula

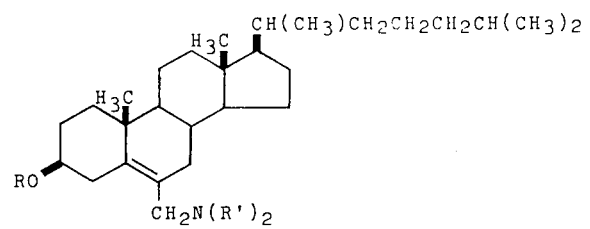

wherein R represents alkanoyl of the formula $C_aH_{2a+1}CO-$ in which $a$ represents a positive integer less than 8, and R' represents alkyl of the formula $C_bH_{2b+1}-$ in which $b$ represents a positive integer less than 8.

4. A compound according to claim 1 which is 3β-acetoxy-6-(diethylaminomethyl)cholest-5-ene.
5. A compound according to claim 1 having the formula

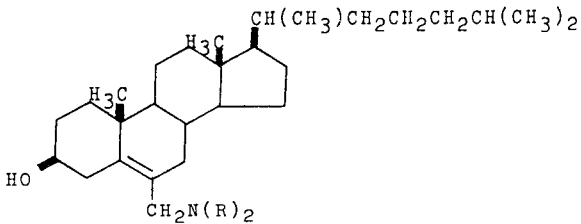

wherein R represents alkyl of the formula $C_aH_{2a+1}-$ in which $a$ represents a positive integer less than 8.

6. A compound according to claim 1 which is 6-(diethylaminomethyl)cholest-5-en-3β-ol.
7. A compound according to claim 1 having the formula

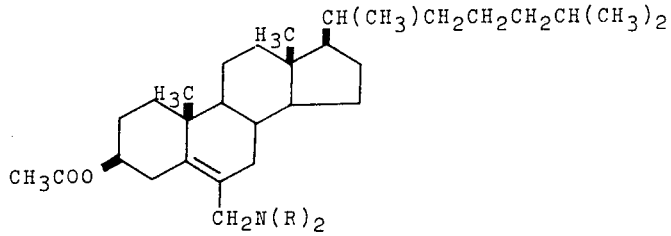

wherein R represents hydroxyalkyl of the formula $HOC_aH_{2a}-$ in which $a$ represents a positive integer greater than 1 and less than 5.

8. A compound according to claim 1 which is 3β-acetoxy-6-[di(2-hydroxyethyl)aminomethyl]cholest-5-ene.
9. A compound according to claim 1 having the formula

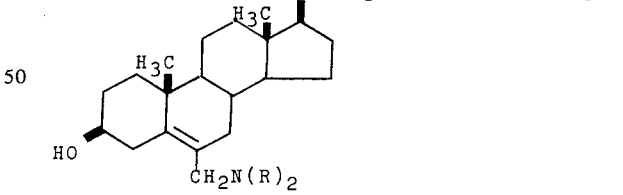

wherein R represents hydroxyalkyl of the formula $HOC_aH_{2a}-$ in which $a$ represents a positive integer greater than 1 and less than 5.

10. A compound according to claim 1 which is 6-[di(2-hydroxyethyl)aminomethyl]cholest-5-en-3β-ol.
11. A compound according to claim 1 having the formula

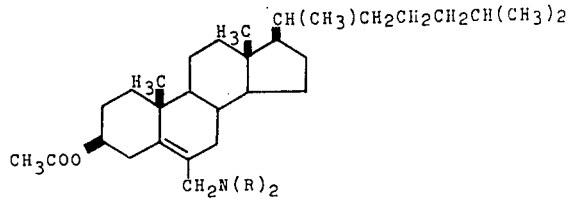

wherein R represents alkoxyalkyl of the formula

in which *a* represents a positive integer greater than 1 and less than 5 and *b* represents a positive integer greater than 1 and less than 4.

12. A compound according to claim 1 which is 3β-acetoxy-6-[di(2-ethoxyethyl)aminomethyl]cholest-5-ene.

13. A compound according to claim 1 having the formula

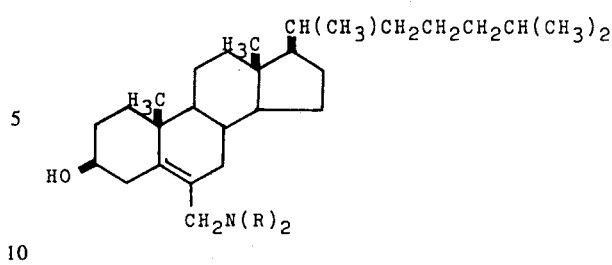

wherein R represents alkoxyalkyl of the formula

in which *a* represents a positive integer greater than 1 and less than 5 and *b* represents a positive integer greater than 1 and less than 4.

14. A compound according to claim 1 which is 6-[di(2-ethoxyethyl)aminomethyl]cholest-5-en-3β-ol.

* * * * *

UNITED STATES PATENT AND TRADEMARK OFFICE
CERTIFICATE OF CORRECTION

PATENT NO. : 3,960,904
DATED : June 1, 1976
INVENTOR(S) : Leonard N. Nysted

It is certified that error appears in the above-identified patent and that said Letters Patent are hereby corrected as shown below:

Column 1, line 23, "droxyalkyl) amino" should read -- droxyalkyl)amino --.

Column 3, line 39, "determined" should read -- demonstrated --.

Column 3, line 46, "in" should read -- for --.

Column 3, line 68, "mcgm ml" should read -- mcgm per ml --.

Column 5, line 7, "275 mµ determined" should read -- 275 mµ are determined --.

Column 7, line 21, "too" should read -- to --.

Column 7, line 50, "3α-acetoxy" should read --3β-acetoxy --.

Column 9, line 68, "62" should read -- 3β --.

Column 12, line 30, "5en" should read -- 5-en --.

Column 13, line 55, "3β-N-" should read -- 3β-hydroxy-N- --.

Column 13, line 56, "6methanaminium" should read -- 6-methanaminium --.

Signed and Sealed this

Thirtieth Day of November 1976

[SEAL]

Attest:

RUTH C. MASON
*Attesting Officer*

C. MARSHALL DANN
*Commissioner of Patents and Trademarks*